US007871633B2

(12) United States Patent
Bekele et al.

(10) Patent No.: US 7,871,633 B2
(45) Date of Patent: Jan. 18, 2011

(54) ANHYDROUS, TRANSFER-RESISTANT COSMETIC LIP COMPOSITIONS

(75) Inventors: Haimanot Bekele, Baltimore, MD (US); Claire Davison, Baltimore, MD (US); Qadira Tayyiba Wagstaff, Baltimore, MD (US); Catherine Joyce Noell, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1275 days.

(21) Appl. No.: 10/824,118

(22) Filed: Apr. 14, 2004

(65) Prior Publication Data
US 2005/0025793 A1 Feb. 3, 2005

Related U.S. Application Data

(60) Provisional application No. 60/462,866, filed on Apr. 14, 2003.

(51) Int. Cl.
*A61K 8/02* (2006.01)
(52) U.S. Cl. .................................................... 424/401
(58) Field of Classification Search ...................... None
See application file for complete search history.

(56) References Cited

U.S. PATENT DOCUMENTS

| | | | |
|---|---|---|---|
| 4,861,907 A | | 8/1989 | Wright et al. |
| 5,164,522 A | | 11/1992 | McCarthy et al. |
| 5,260,055 A | | 11/1993 | Imperante et al. |
| 5,262,150 A | | 11/1993 | Laugier et al. |
| 5,372,804 A | | 12/1994 | Khoshdel et al. |
| 5,503,824 A | | 4/1996 | Lentini et al. |
| 5,578,298 A | | 11/1996 | Berthiaume et al. |
| 5,635,163 A | | 6/1997 | Hansenne |
| 5,900,393 A | | 5/1999 | Ramachandran et al. |
| 5,925,341 A | | 7/1999 | Cervantes et al. |
| 6,010,709 A | * | 1/2000 | Nichols ........................ 424/401 |
| 6,045,782 A | | 4/2000 | Krog et al. |
| 6,110,451 A | | 8/2000 | Matz et al. |
| 6,139,823 A | | 10/2000 | Drechsler et al. |
| 6,153,567 A | | 11/2000 | Hughes |
| 6,159,914 A | | 12/2000 | DeCoster et al. |
| 6,180,117 B1 | | 1/2001 | Berthiaume et al. |
| 6,251,413 B1 | | 6/2001 | Ferrari et al. |
| 6,268,454 B1 | | 7/2001 | Song et al. |
| 6,451,905 B2 | | 9/2002 | Spyropoulos et al. |
| 6,706,836 B1 | | 3/2004 | Holguin et al. |
| 2001/0031270 A1 | | 10/2001 | Douin et al. |
| 2001/0051142 A1 | | 12/2001 | Duden et al. |
| 2002/0006389 A1 | | 1/2002 | Restle et al. |
| 2003/0157049 A1 | * | 8/2003 | Gawtrey et al. ........ 424/70.122 |
| 2003/0228267 A1 | | 12/2003 | Aust et al. |

FOREIGN PATENT DOCUMENTS

| | | |
|---|---|---|
| EP | 0 445 700 B1 | 9/1991 |
| EP | 0 529 883 A1 | 3/1993 |
| EP | 0829254 A1 | 3/1998 |
| EP | 1356800 A2 | 10/2003 |
| JP | 57058605 A2 | 4/1982 |
| JP | 05017333 A2 | 1/1993 |
| JP | 05032527 A2 | 2/1993 |
| JP | 05032534 A2 | 2/1993 |
| JP | 05098161 A2 | 4/1993 |
| JP | 08027273 A2 | 1/1996 |
| JP | 08092029 A2 | 4/1996 |
| JP | 08257391 A2 | 10/1996 |
| JP | 09095419 A2 | 4/1997 |
| JP | 10095705 A2 | 4/1998 |
| JP | 10245330 A2 | 9/1998 |
| JP | 2000128768 A2 | 5/2000 |
| JP | 2000178125 A2 | 6/2000 |
| JP | 01002925 A | 1/2001 |
| JP | 2001002925 A2 | 1/2001 |
| JP | 2001081009 A2 | 3/2001 |
| JP | 2001131580 A2 | 5/2001 |
| JP | 2001/302456 A | 10/2001 |
| JP | 2002060331 A2 | 2/2002 |
| WO | WO 96/19185 | 6/1996 |
| WO | WO 00/28964 | 5/2000 |
| WO | WO 01/41721 A1 | 6/2001 |
| WO | WO 01/62376 A1 | 8/2001 |
| WO | WO 01/74917 A1 | 10/2001 |
| WO | WO 01/76552 A3 | 10/2001 |
| WO | WO 03/086333 A1 | 10/2003 |

OTHER PUBLICATIONS

Product Information (Personal Care) Dow Corning 2-8566 Amino Fluid (accessed Sep. 21, 2010) http://www4.dowcorning.com/DataFiles/090007c8800042c8.pdf.*

* cited by examiner

*Primary Examiner*—Robert A Wax
*Assistant Examiner*—Devesh Srivastava
(74) *Attorney, Agent, or Firm*—Megan C. Hymore; S. Robert Chuey; Carl Roof

(57) ABSTRACT

The anhydrous cosmetic composition of the present invention provides a durable film after application that resists degradation over time. The anhydrous cosmetic composition includes an aminosilicone, an organosiloxane resin, a diorganopolysiloxane polymer and a volatile carrier. The anhydrous cosmetic composition can also be packaged with a topcoat product.

12 Claims, No Drawings

ANHYDROUS, TRANSFER-RESISTANT COSMETIC LIP COMPOSITIONS

CROSS REFERENCE TO RELATED APPLICATIONS

This application claims the benefit under 35 USC 119(e) to U.S. Application Ser. No. 60/462,866, filed Apr. 14, 2003.

TECHNICAL FIELD

The present invention relates to anhydrous, transfer-resistant cosmetic lip compositions suitable for application to lips that comprise modified silicones, particularly, aminosilicones, epoxy modified and carboxy modified silicones, an organosiloxane resin, a definitive diorganopolysiloxane polymer, and a volatile carrier. Upon application the composition forms a thin, but, durable film resistant to transfer upon contact with objects such as clothing, towels, cups, handkerchiefs and tissues. The present invention also relates to methods of enhancing performance and/or appearance by the addition of modified silicone fluids in long wearing lip color products.

BACKGROUND

Transfer resistant lip products have gained increasing popularity over the last decade as consumers find themselves consumed with the stress of daily activities. These types of products allow consumers to apply the lip product fewer times in a day but still achieve a freshly applied appearance. One shortcoming of a number of these products, however, has been the undesirable feel and quality of wear on the lips that accompanies the use of such products. For example, consumers complain of a tight feeling on the lips that typically results from the inclusion of film forming agents into these products that provides the long wear characteristic. Additionally, consumers complain of the quality of wear of the lip color indicating that the color does not last throughout the day, i.e., the color does not retain a freshly applied, consistent look over an extended period of time. Thus, there remains a need for a lip product that not only provides a more pleasurable feel when applied and worn on the lips but, at the same time, provides a long, fresh-look wear for the consumer. Compositions of the present invention not only provide profound film resistant to transfer upon contact with objects such as clothing, towels, cups, handkerchiefs and tissues throughout the day, but also provides the qualifies to maintaining a freshly applied, consistent look. Additionally, appearance benefits such as gloss and shine are exemplified in a single step application of the invention.

SUMMARY OF THE INVENTION

The cosmetic compositions of the present invention provide a durable film after application that resists degradation over time. Cosmetic compositions of the present invention comprise:
(A) an anhydrous mixture of:
  (1) modified silicones selected from the group consisting of aminosilicones, carboxy modified silicones, epoxy modified silicones, and mixtures thereof;
  (2) an organosiloxane resin;
  (3) a diorganopolysiloxane polymer; and
(B) a volatile carrier.

DETAILED DESCRIPTION

The compositions of the present invention are anhydrous, transfer-resistant lip cosmetic compositions. Lip products comprising the cosmetic compositions of the present invention exhibit a viscosity of from about 500 cP to about 15,000 cP, preferably from about 500 cp to about 8,000 cP, more preferably from about 1,000 cP to about 5,000 cP.

Applicants have found that compositions as detailed herein are particularly resistant against insult when subjected to the typical rigors of daily lip exposure.

As used herein, "comprising" means that other steps and ingredients can be added. This term encompasses the terms "consisting of" and "consisting essentially of". The phrase "consisting essentially of" means that the composition may include additional ingredients, but only if the additional ingredients do not materially alter the basic and novel characteristics of the claimed compositions or methods.

All percentages, parts and ratios are based upon the total weight of the topical compositions of the present invention and all measurements made are at 25° C., unless otherwise specified. All such weights as they pertain to listed ingredients are based on the active level and, therefore, do not include carriers or by-products that may be included in commercially available materials, unless otherwise specified.

All publications cited herein are hereby incorporated by reference in their entirety.

As used herein, "lip product" means a cosmetic that can be applied to the lips and may be in the form of a liquid, conventional bullet, gel, cream, lip color pen, and the like.

The compositions of the present invention necessarily comprise the following ingredients.

Modified Silicones

The compositions of the present invention comprise modified silicones. Particularly, the modified silicones are selected from the group consisting of aminosilicones, carboxy modified silicones, epoxy modified silicones and mixtures thereof. Modified silicones useful in the present invention have the following general structure wherein R can be selected from the group consisting of amino, epoxy or carboxy groups:

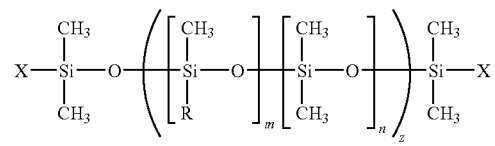

Aminosilicone R=—R'NH$_2$ or R=R'NHR"NH$_2$
Epoxy modified

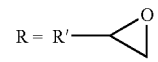

Carboxy modified R=R'COOH
R' and R"=ethylene, propylene, isobutylene, butylene, isopropylene, alkylene, cycloalkylene alkylene ether
X=CH$_3$, OCH$_3$, R, or a combination thereof
wherein m is 1-5, preferably 1-3, n is 10-100, and z is 8-450.

The modified silicones are used in the present invention at levels from about 0.1% to about 70%, preferably from about 0.5% to about 50% and most preferably from about 0.5% to about 30% of the total amount of the cosmetic composition. It is preferred that the modified silicones are present at a viscosity of from about 100 cSt to about 2,000,000 cSt at 25° C., preferably from about 2,000 cSt to 2,000,000 cSt at 25° C.

Additionally, compositions of the present invention may comprise silicone modified fluorinated polymers used alone or in combination with the modified silicones disclosed above.

Organosiloxane Resin

The compositions of the present invention comprise an organosiloxane resin. The resin may comprise combinations of $R_3SiO_{1/2}$ "M" units, $R_2SiO$ "D" units, $RSiO_{3/2}$ "T" units, $SiO_2$ "Q" units in ratios to each other that satisfy the relationship $R_nSiO_{(4-n)/2}$ where n is a value between 1.0 and 1.50 and R is a methyl group. Up to 5% of silanol or alkoxy functionality may also be present in the resin structure as a result of processing. The organosiloxane resins have a number molecular weight average range of from about 1,000 g/mole to about 10,000 g/mole. The resin is soluble in organic solvents such as toluene, xylene, isoparaffins, and cyclosiloxanes or the volatile carrier, indicating that the resin is not sufficiently crosslinked such that the resin is insoluble in the volatile carrier. Particularly preferred are resins comprising repeating monofunctional or $R_3SiO_{1/2}$ "M" units and the quadrafunctional or $SiO_2$ "Q" units, otherwise known as "MQ" resins as disclosed in U.S. Pat. No. 5,330,747, Krzysik, issued Jul. 19, 1994, incorporated herein by reference. In the present invention the ratio of the "M" to "Q" functional units is about 0.6 to about 2.0, more preferably about 0.6 to about 0.9, most preferably about 0.7. Examples of organosiloxane resins commercially available are WACKER 803 and WACKER 804 available from Wacker Silicones Corporation of Adrian Mich., and G.E. SR1000 from the General Electric Company.

The organosiloxane resins are used in the present invention at levels from about 10% to about 95%, preferably from about 55% to about 80%, and most preferably 60% to about 70% of the total amount of organosiloxane resin, diorganopolysiloxane polymers and modified silicones.

Diorganopolysiloxane Polymer

The present invention may also employ a diorganopolysiloxane polymer that is combined with the organosiloxane resin disclosed above. Applicants have found that suitable polymers exhibit a viscosity of at least about 1,000,000 cSt at 25° C.

The diorganopolysiloxane polymers of the present invention comprise repeating units, wherein said units correspond to the formula $(R_2SiO)$, where R is a monovalent hydrocarbon radical containing from 1 to 6 carbon atoms, preferably selected from the group consisting of methyl, ethyl, propyl, isopropyl, butyl, isobutyl, t-butyl, amyl, hexyl, vinyl, allyl, cyclohexyl, phenyl, fluoroalkyl and mixtures thereof. The diorganopoylsiloxanes employed in the present invention may contain one or more of these hydrocarbon radicals as substituents on the siloxane polymer backbone. The diorganopolysiloxanes may be terminated by triorganosilyl groups of the formula $(R'_3Si)$ where R' is a radical selected from the group consisting of monovalent hydrocarbons containing from 1-6 carbon atoms, hydroxyl groups, alkoxyl groups and mixtures thereof. When a diorganopolysiloxane polymer is present, it is essential that it be compatible in the mixture with the organosiloxane resin material and the volatile carrier. The term "compatible" refers to the formation of a homogeneous blend when the diorganopolysiloxane, organosiloxane resin and volatile carrier are mixed together in ratios required for a specific formulation. A particularly preferred diorganopolysiloxane polymer is poly(dimethylsiloxane), herein referred to as PDMS. Suitable diorganopolysiloxane polymers have the following structural formula wherein n is equal to from about 1500 to about 4500:

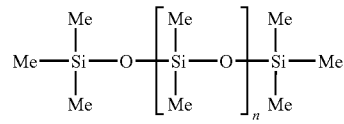

Volatile Carrier

In the present invention, the combination of the organosiloxane resin and diorganosiloxane polymer above must be easily transferred to the lip surface using a package/applicator. To achieve delivery, it is necessary that this combination above be incorporated into a carrier, specifically a volatile carrier which quickly volatilizes from the surface of the lips leaving the above-discussed thin-durable film. The volatile carrier must solubilize the organosiloxane resin and the diorganosiloxane polymer.

The volatile carrier comprises from about 10% to about 90%, preferably from about 15% to about 80%, and most preferably from about 20% to about 70% of the composition. The volatile carrier of the present invention are selected from the group consisting of volatile hydrocarbons, volatile silicones and mixtures thereof.

Hydrocarbon oils useful in the present invention include those having boiling points in the range of 60-260° C., more preferably hydrocarbon oils having from about $C_5$ to about $C_{20}$ chain lengths, most preferably $C_7$ to $C_{16}$ isoparaffins. Of these isoparriffins most preferred are selected from the group consisting of isododecane, isohexadecane, isoeocosane, 2,2,4-trimethylpentane, 2,3-dimethylhexane and mixtures thereof. Most preferred is isododecane, which is also known as 2,2,4,6,6-pentamethylheptane. Isododecane that is suitable for inclusion in the compositions of the present invention is available from a number of sources, e.g., from Presperse, Inc. as PERMETHYL 99A.

Preferred volatile silicone fluids include cyclomethicones having 4, 5, and 6 member ring structures corresponding to the formula:

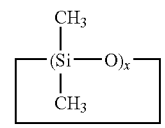

where X is from about 3 to about 6. Said volatile silicones include 244 Fluid, 344 Fluid and 245 Fluid, and 345 Fluid all from Dow Corning Corporation.

Thickeners/Structure Builders

The cosmetic composition of the present invention may also comprise at least one of the group consisting of thickeners or structure builders which have the function of dispersing pigments in addition to building viscosity. Thickeners and/or structure builders useful for the present invention include, but are not limited to, organically modified clays, fumed silica, silgels or silicone elastomers, alkyl silicone waxes, silicone polyamide, trihydroxystearin, diblock/triblock copolymers and silsequioxane crosspolymers. Organically modified clays useful for the present invention include, but are not limited to, hectorite, bentonite, smectite and montmorillonite clay.

When organically modified clays are present, the compositions comprise less than about 10%, by weight of the composition, more preferably, less than about 5%, and most preferably from about 1% to about 3%.

Pigments

Pigments suitable for use herein are all inorganic and organic colors/pigments suitable for use in lip composition compositions. These are usually aluminum, barium or calcium salts or lakes. Lakes are either a pigment that is extended or reduced with a solid diluent or an organic pigment that is prepared by the precipitation of a water-soluble dye on an adsorptive surface, which usually is aluminum hydrate. A lake also forms from precipitation of an insoluble salt from an acid or basic dye. Calcium and barium lakes are also used herein.

Preferred lakes of the present invention are Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake, Red 30 Talc Lake, and Red 30 Aluminum Lake.

Other colors and pigments can also be included in the lip compositions, such as dyes and pearls, titanium oxides, Red 6, Red 21, Blue 1, Orange 5, and Green 5 dyes, chalk, talc, iron oxides and titanated micas.

Compositions of the present invention contain sufficient pigments to provide the look sought by the user. The pigments are used herein at levels relative to the level of the diorganopolysiloxane polymers disclosed above. This level is expressed as a ratio of the combination of diorganopolysiloxane polymer and organosiloxane resin to pigment. In the present invention this ratio is from about 1:1 to about 30:1, preferably from about 1.5:1 to about 15:1, and most preferably from about 2:1 to about 10:1.

Additionally, the cosmetic compositions of the present invention are anhydrous. As used herein "anhydrous" means that the compositions comprise less than about 5%, by weight of the composition, of water, more preferably less than about 2%, and even more preferably less than about 1%.

Waxes

Waxes may be used in the present invention provided they are used at levels which does not interfere with film formation process.

Waxes are defined as lower-melting organic mixtures or compounds of high molecular weight, solid at room temperature and generally similar in composition to fats and oils except that they contain no glycerides. Some are hydrocarbons, others are esters of fatty acids and alcohols. Waxes useful in the present invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof.

The specific waxes useful in the present invention are selected from the group consisting of synthetic waxes, ozokerite, jojoba esters, "Unilins", available from Petrolite Corporation, "Ganex" alkylated polyvinylpyrrolidines available from the ISP Company, fatty alcohols from C22 to C50 and mixtures thereof. Synthetic waxes include those disclosed in Warth, *Chemistry and Technology of Waxes*, Part 2, 1956, Reinhold Publishing; herein incorporated by reference. The waxes most useful herein are selected from the $C_8$ to $C_{50}$ hydrocarbon waxes. Such waxes include long chained polymers of ethylene oxide combined with a dihydric alcohol, namely polyoxyethylene glycol. Such waxes include CARBOWAX available from Carbide and Carbon Chemicals company. Other synthetic waxes include long-chained polymers of ethylene with OH or other stop length grouping at end of chain. Such waxes include the Fischer-Tropsch waxes as disclosed in the text disclosed above at pages 465-469 and include ROSSWAX, available from Ross company and PT-0602 available from Astor Wax Company.

The cosmetic compositions of the present invention are also in the form of liquid lip products. As such, the compositions comprise less than about 2%, by weight of the composition, of waxes, more preferably, less than about 1%, and most preferably less than about 0.5%.

Other Ingredients

There are a number of other ingredients approved for use in the cosmetic art that may be used in compositions of the present invention. Such ingredients are those approved for use in cosmetics and can be found listed in reference books such as the CTFA Cosmetic Ingredient Handbook, Second Edition, The Cosmetic, Toiletries, and Fragrance Association, Inc. 1988, 1992. Said materials may be used provided their inclusion does not significantly disrupt the composition once it has been applied wherein a film has been formed. Said ingredients include waxes, fragrances, flavor oils, skin care ingredients such as sunscreen, emulsifiers and the like. Hypoallergenic compositions can be made into the present invention where said compositions do not contain fragrances, flavor oils, lanolin, sunscreens, particularly PABA, or other sensitizers and irritants.

Complimentary products may be used in conjunction with the present invention to compliment the composition and improve its aesthetic appeal to the user. In particular, it is intended that the cosmetic compositions of the present invention may be paired in a lip cosmetic kit with such a complementary product.

It is specifically envisioned that the complementary products used in the present invention manner wherein such a product is applied over the film formed after application of the cosmetic composition of the present invention. For example in the case of lip compositions, a complimentary product may be utilized to enhance the gloss and shine of the lips and provide a lubricious feeling. Such products, otherwise known as an "overcoat" or "topcoat" may be in a stick or liquid form and can include any that are commercially available or to be developed, provided the aggregate of the materials comprising the overcoat does not significantly disrupt the composition of the present invention. The overcoat compositions may be clear or transparent or may contain dyes and/or colorants that when viewed along with the overcoat, produce a desired color.

One such material that has been shown to be quite useful in formulating complimentary products is polyol polyesters, such as sucrose polyesters (herein referred to as SPE'S). SPE's are synthesized molecules derived from sugar and vegetable oil and have been extensively disclosed in the patent literature in context of a non-digestible oils. Such compositions are generally disclosed in U.S. Pat. No. 3,600,186, issued Aug. 17, 1971; U.S. Pat. No. 4,005,195, issued Jan. 25, 1977; U.S. Pat. No. 4,005,196, issued Jan. 25, 1977; all assigned to the Procter & Gamble Company and all herein incorporated by reference.

It has found that overcoat compositions having a significant level of SPE'S are incompatible with the lip composition of the present composition wherein upon their application, the cosmetic composition of the present invention is not disrupted.

In a preferred embodiment of the present invention, a complementary product comprising a topcoat composition comprises a safe and effective amount of a polymeric vegetable oil emollient. More preferably, the polymeric vegetable oil emollient is a copolymer of Brassica Campestris and Aleurites Fordii oil (also known as polytriglyceryl erucate/eliostearate), which is an unsaturated complex ester ranging in molecular weight from 25,000 to 110,000 (or 6500 to about 7500 daltons). This emollient is commercially available from Tri-K under the tradename GLOSSAMER L-6600 and allows the topcoat to form a protective film over the cosmetic compositions of the present invention. Such a topcoat composition aids in providing a creamier feel to the applied basecoat and topcoat and also enhances the water and rub-off resistance of the cosmetic composition as well as the topcoat composition. In more preferred embodiments, the polymeric vegetable oil emollient is present in an amount of from about 0.1% to about 50%, more preferably, from about 2% to about 20%, and most preferably, from about 4% to about 15%, by weight of the topcoat composition.

Modified silicones of the present invention may also be used as topcoats. Additionally, silicone modified fluorinated polymers may be used alone or in combination with the modified silicones of the present invention as topcoats.

Method of Using the Invention

The method of the present invention is straightforward. The user applies the composition of the present invention from a suitable liquid cosmetic applicator directly onto the skin. One such applicator used for liquid lip products is a liquid pen package disclosed in British Patent 21198037, issued May 9, 1990, assigned to Mitsubishi Pencil Co., Ltd. of Japan. An alternative package is one where an wand is dipped into a reservoir wherein the composition on the tip of the wand is applied to the skin surface. Such packages are disclosed in Japanese Utility Model 64 000822 Y2, to Shiseido.

Another cosmetic dispenser that is useful for the present invention is a unidirectional twist-up dispensing device with incremental dosing as disclosed in U.S. Pat. No. 5,851,079, issued on Dec. 22, 1998 to Richard L. Horstman et al. Such a twist-up dispensing device can include a hollow housing defining a chamber having an open dispensing end and a piston located within the chamber being limited to translational movement within the chamber. The piston preferably having a threaded rod extending therefrom that engages with a threaded aperture in an actuator such that advancement of the piston toward the dispensing end occurs when the actuator is rotated. Rotation of the actuator causes the product to be dispensed from the dispensing end. An applicator is preferably attached to the dispensing end of the housing in fluid communication with the chamber wherein the product is dispensed through the applicator. The applicator can comprise a ferrule and an application portion wherein the ferrule is attached to the dispensing end of the housing and the application portion has at least one orifice located therein. Several versions of applicators can be utilized including, for example, a fiber brush or an application surface having flocking thereon. Flocking is a mat of thin, short, plastic fibers substantially perpendicular to the application surface. The bristles of a fiber brush are preferably tapered and made of a plastic material. Alternatively, the user may use a more traditional applicator or implement known in the art.

As stated above, the user applies the composition wherein the user allows the composition to dry before subjecting the composition to insult. Once the composition is dried, a complimentary product such as the topcoat product disclosed above may be applied over the dried product to provide the user with an asthetically pleasing affect. Topcoat compositions may utilize the same dispensing device as described for use of the compositions of the present invention.

The compositions of the present invention may be removed by applying petrolatum or a dimethicone-based cosmetic remover and by rubbing the area gently with a tissue to remove the cosmetic.

EXAMPLES

The following examples illustrate the claimed cosmetic compositions of the present invention but are not intended to be limiting thereof:

Example 1

| Ingredients | Weight (%) |
| --- | --- |
| Group A: | |
| Polydimethylsiloxane[1] | 10 |
| Bentone Gel[2] | 20 |
| Isododecane[3] | 30 |
| Aminosilicone[4] | 10 |
| Group B: | |
| Organosiloxane Resin[5] | 15 |
| Red #7 Calcium Lake | 5 |
| Titanated Mica[6] | 3 |
| Titanium Dioxide | 1.5 |
| Black Iron Oxide | .5 |

[1]300,000 cSt polydimethylsiloxane available as DM300000 from Wacker Silicones. May also substitute polydimethylsiloxanes with viscosities at 25° C. of 400,000 cSt, 500,000 cSt, 600,000 cSt, 700,000 cSt, 800,000 cSt, 900,000 cSt, 1,000,000 cSt.
[2]Bentone Gel ISD available from Elementis
[3]Permethyl 99A available from Permethyl Corporation.
[4]Aminosilicone available from Dow Corning as DC 2-8566
[5]MQ Resin (0.7:1 M:Q) available as SR1000 from General Electric
[6]Flamenco Superpearl available from Engelhard
Combine Group A ingredients together in a beaker and mix with a propeller mixer until the mixture is homogeneous. Add Group B ingredients to the Group A Mixture and drymix the mixture to roughly incorporate the dry powders. Then homogenize the formulation until all pigments are full dispersed. Transfer the resulting fluid to individual packages.

Example 2

| Ingredients | Weight (%) |
| --- | --- |
| Group A: | |
| Polydimethylsiloxane[1] | 8 |
| Bentone Gel[2] | 20 |
| Isododecane[3] | 30 |
| Epoxysilicone[4] | 10 |
| Group B: | |
| Organosiloxane Resin[5] | 17 |
| Red #7 Calcium Lake | 7 |
| Titanated Mica[6] | 5 |
| Titanium Dioxide | 2.5 |
| Black Iron Oxide | 0.5 |

[1]300,000 cSt polydimethylsiloxane available as DM300000 from Wacker Silicones. May also substitute polydimethylsiloxanes with viscosities at 25° C. of 400,000 cSt, 500,000 cSt, 600,000 cSt, 700,000 cSt, 800,000 cSt, 900,000 cSt, and 1,000,000 cSt.
[2]Bentone Gel ISD available from Elementis
[3]Permethyl 99A available from Permethyl Corporation.
[4]Epoxysilicone available from Shin-Estu as KF-1001
[5]MQ Resin (0.7:1 M:Q) available as SR1000 from General Electric
[6]Flamenco Superpearl available from Engelhard
Combine Group A ingredients together in a beaker and mix with a propeller mixer until the mixture is homogeneous. Add Group B ingredients to the Group A Mixture and drymix the mixture to roughly incorporate the dry powders. Then homogenize the formulation until all pigments are full dispersed. Transfer the resulting fluid to individual packages.

Example 3

| Ingredients | Weight (%) |
| --- | --- |
| Group A: | |
| Polydimethylsiloxane[1] | 0.5 |
| Bentone Gel[2] | 20 |
| Isododecane[3] | 30 |
| Aminosilicone[4] | 9.5 |
| Group B: | |
| Organosiloxane Resin[5] | 20 |
| Red #7 Calcium Lake | 10 |
| Titanated Mica[6] | 6 |
| Titanium Dioxide | 3 |
| Black Iron Oxide | 1 |

[1]300,000 cSt polydimethylsiloxane available as DM300000 from Wacker Silicones. May also substitute polydimethylsiloxanes with viscosities at 25° C. of 400,000 cSt, 500,000 cSt, 600,000 cSt, 700,000 cSt, 800,000 cSt, 900,000 cSt, 1,000,000 cSt.
[2]Bentone Gel ISD available from Elementis
[3]Permethyl 99A available from Permethyl Corporation.
[4]Aminosilicone available from Dow Corning as Dc 2–8566
[5]MQ Resin (0.7:1 M:Q) available as SR1000 from General Electric
[6]Flamenco Superpearl available from Engelhard Combine Group A ingredients together in a beaker and mix with a propeller mixer until the mixture is homogeneous. Add Group B ingredients to the Group A Mixture and drymix the mixture to roughly incorporate the dry powders. Then homogenize the formulation until all pigments are full dispersed. Transfer the resulting fluid to individual packages.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An anhydrous cosmetic composition comprising:
(A) an anhydrous mixture of:
(1) an aminosilicone with the structure:

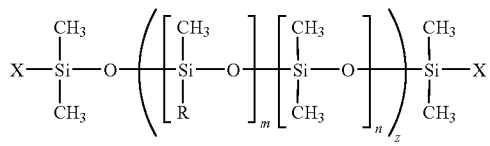

wherein X is $CH_3$; wherein R is $NHCH_2CH_2NH_2$; wherein m is 1 to 5; wherein n is 10 to 100; and wherein z is 8 to 450; and
(2) an organosiloxane resin; and
(3) a diorganopolysiloxane polymer; and
(B) a volatile carrier.

2. The cosmetic composition of claim 1, further comprising the group consisting of thickeners and structure builders, wherein the thickeners and structure builders are selected from the group consisting of organically modified clays, fumed silica, silgels, alkyl silicone waxes, silicone polyamide, diblock/triblock copolymers and silsequioxane crosspolymers.

3. The cosmetic composition of claim 2, wherein the organically modified clay is selected from the group consisting of hectorite, bentonite, smectite, montmorillonite clay, and mixtures thereof.

4. The cosmetic composition of claim 1, wherein the organosiloxane resin comprises $R_3SiO_{1/2}$ "M" units, $R_2SiO$ "D" units, $RSiO_{3/2}$ "T" units, $SiO_2$ "Q" units and mixtures thereof in a ratio selected to satisfy the relationship $R_nSiO_{(4-n)/2}$, wherein n is from about 1.0 to about 1.50 and R is a methyl group.

5. The cosmetic composition of claim 1, wherein the organosiloxane resin comprises $R_3SiO_{1/2}$ "M" units and $SiO_2$ "Q" units wherein the ratio of $R_3SiO_{1/2}$ to $SiO_2$ is about 0.6 to about 2.0.

6. The cosmetic composition of claim 1, wherein the aminosilicone has a viscosity of from about 100 cSt to about 2,000,000 cSt at 25° C.

7. The cosmetic composition of claim 1, wherein the diorganopolysiloxane polymer has a viscosity of from at least about 1,000,000 cSt at 25° C.

8. The cosmetic composition of claim 1, wherein the volatile carrier is selected from the group consisting of volatile hydrocarbon, volatile silicone, and mixtures thereof.

9. The cosmetic composition of claim 8, wherein the volatile carrier is isododecane.

10. The cosmetic composition of claim 1, wherein the composition is paired with a topcoat product comprising a safe and effective amount of modified silicones selected from the group consisting of aminosilicones, carboxy modified silicones, epoxy modified silicones, and mixtures thereof.

11. The cosmetic composition of claim 1, wherein the composition is paired with a topcoat product comprising a safe and effective amount of a polymeric vegetable oil emollient.

12. The cosmetic composition of claim 1, wherein the composition is paired with a topcoat product comprising a safe and effective amount of a silicone modified fluorinated polymer.

* * * * *